US010086029B2

(12) United States Patent
Houle et al.

(10) Patent No.: US 10,086,029 B2
(45) Date of Patent: *Oct. 2, 2018

(54) FERMENTED PLANT EXTRACTS, METHODS OF PRODUCTION AND USES

(71) Applicant: KEFIPLANT INC., Drummondville (CA)

(72) Inventors: Chantale Houle, Drummondville (CA); Serge Rollan, Pamiers (FR); Christian Deshayes, Toulouse (FR)

(73) Assignee: KEFIPLANT INC., Drummondville, QC (CA)

( * ) Notice: Subject to any disclaimer, the term of this patent is extended or adjusted under 35 U.S.C. 154(b) by 412 days.

This patent is subject to a terminal disclaimer.

(21) Appl. No.: 14/690,573

(22) Filed: Apr. 20, 2015

(65) Prior Publication Data

US 2015/0224158 A1   Aug. 13, 2015

Related U.S. Application Data

(63) Continuation-in-part of application No. 12/308,409, filed as application No. PCT/CA2007/001068 on Jun. 15, 2007, now Pat. No. 9,044,399.

(60) Provisional application No. 60/814,045, filed on Jun. 16, 2006, provisional application No. 60/924,275, filed on May 7, 2007.

(51) Int. Cl.

| C12P 1/00 | (2006.01) |
|---|---|
| A23B 7/10 | (2006.01) |
| A23F 3/00 | (2006.01) |
| A01N 65/00 | (2009.01) |
| A61K 36/00 | (2006.01) |
| A61K 36/82 | (2006.01) |
| A61K 36/28 | (2006.01) |
| A61K 36/53 | (2006.01) |
| A61K 36/84 | (2006.01) |
| A61K 35/20 | (2006.01) |
| A23L 33/105 | (2016.01) |

(52) U.S. Cl.
CPC ............ *A61K 36/53* (2013.01); *A23L 33/105* (2016.08); *A61K 35/20* (2013.01); *A61K 36/84* (2013.01); *A61K 2236/19* (2013.01)

(58) Field of Classification Search
None
See application file for complete search history.

(56) References Cited

U.S. PATENT DOCUMENTS

| 4,996,064 A * | 2/1991 | Akano ............... A23L 11/09 |
|---|---|---|
| | | 426/46 |
| 5,486,367 A * | 1/1996 | Fung ................. A21D 8/042 |
| | | 426/10 |
| 6,103,875 A * | 8/2000 | Martinez-Miller .... C07K 14/21 |
| | | 530/359 |
| 2003/0185811 A1 | 10/2003 | Teasdale et al. |
| 2003/0211218 A1* | 11/2003 | Cote ...................... A23C 9/123 |
| | | 426/583 |
| 2005/0089499 A1 | 4/2005 | Moussou et al. |

FOREIGN PATENT DOCUMENTS

| EP | 1275308 | 1/2003 |
|---|---|---|
| EP | 1279727 | 1/2003 |
| EP | 1702517 | 9/2006 |
| RO | 118260 | 4/2003 |
| RU | 2270568 | 2/2006 |
| WO | 0195917 | 12/2001 |
| WO | 03/059368 | 7/2003 |
| WO | 2005/009405 | 2/2005 |

OTHER PUBLICATIONS

Holley, et al., "Improvement in shelf-life and safety of perishable foods by plant essentials oils and smoke antimicrobials", Food Microbiology, Aug. 1, 2005, pp. 273-292, vol. 22, No. 4, Elsevier.
Ahmed A. Ismaiel, Mohamed F. Ghaly and Ayman K. El-Naggar, Some physiochemical analyses of kefir produced under different fermentation conditions, Journal of Scientific & Industial Research, vol. 70, May 2011, pp. 365-372.
D.M. Beshkova, E.D. Simova, G.I. Frengova, Z.I. Simov, Zh.P. Dimitrov, Production of volatile aroma compounds by kefir starter cultures, International Dairy Journal, vol. 13, 2003, pp. 529-535.
Je-Ruei Liu and Chin-Wen Lin, Production of Kefir from Soymilk, With or Without Added Glucose, Lactose, or Sucrose, Journal of Food Science, vol. 65, No. 4, 2000, 716-719.
Surmen-Gur, E, Gulten T, Serdar Z, Colakogullan M., "Chronic black tea administration protects plasma proteins, plama, liver and kidney lipids against oxidation." Med Sci Monit, 2006: 12(3):BR102-105. PMID: 16501415.
Kwon, Y, Apostolldis, E., Shetty K., "Anti-Diabetes Functionality of Kefir Culture-Mediated Fermented Soymilk Supplemented with Rhodiola Extracts." Food Biotechnology, 2006, vol. 20, pp. 13-20.
Woodhouse, M. "Migraine and tension headache—a complementary and alternative medicine approach." Australian Family Physician, 2005, vol. 34, No. 8, pp. 647-651.
Mishra, K. et al. "Aqueous Extract of Rodiola imbricata Rhizome Stimulates Proinflammatory Mediators via Phosphorylated . . . Factor-kB." Immunopharmacology and Immunotoxicology, 28:201-212, 2006.
Garro, M. et al. "Growth characteristics and fermentation products of *Streptococcus salivarious* subsp. *thermophilus*, Lactobacillus casei and L. fermentum in soymilk." Z Lebensm Unters Forsch A. 1998, 206: 72-75.
International Search Report PCT/EP03/00066 dated Sep. 4, 2003.
International Search Report PCT/CA2007/00168 dated Oct. 5, 2007.

* cited by examiner

*Primary Examiner* — Chris R Tate
*Assistant Examiner* — Douglas F White

(57) ABSTRACT

The present disclosure concerns plant extracts which have been fermented with kefir grains, methods of production of these extracts, a powder comprising these extracts and compositions comprising these extracts. Since these extracts have a high content of aglycone active principles, their biological activities are high and their applications are varied.

9 Claims, 9 Drawing Sheets

Aqueous extract of *Thymus vulgaris* (CPG/SM and IR identifications)

Aqueous extract of kefirated *Thymus vulgaris* (CPG/SM and IR identifications)

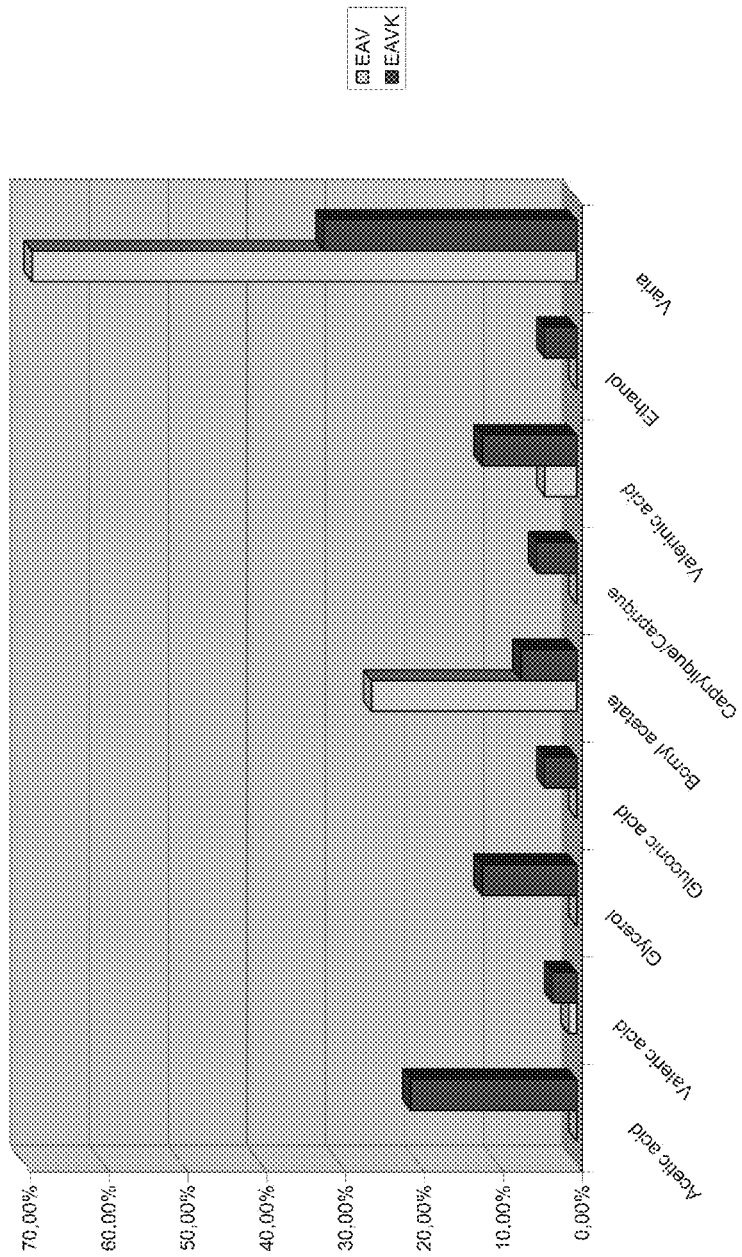

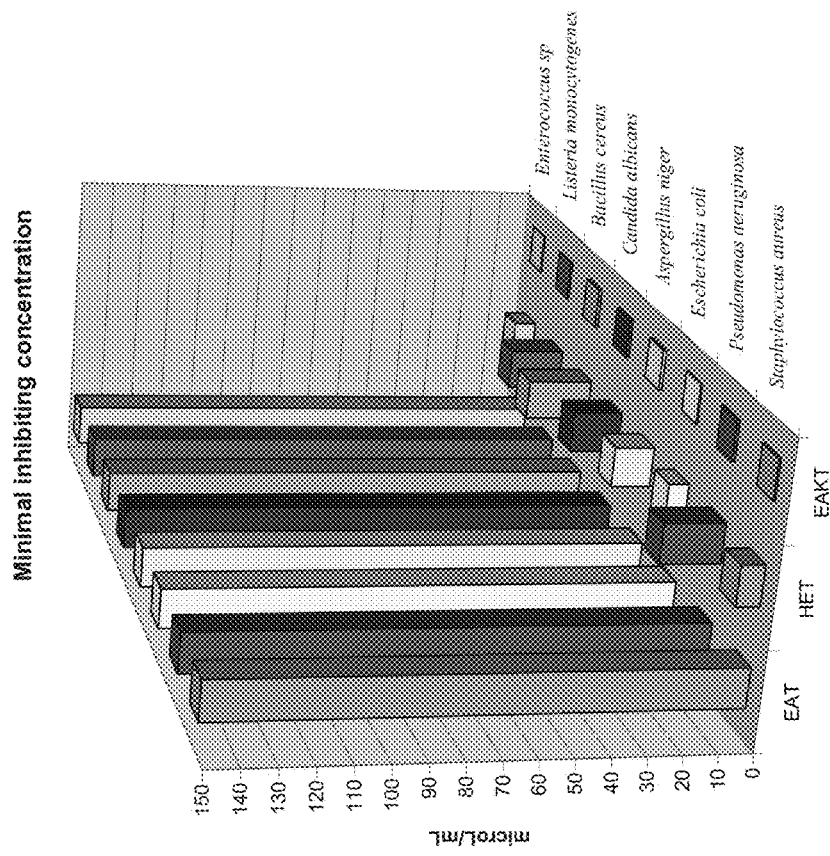

FERMENTED PLANT EXTRACTS, METHODS OF PRODUCTION AND USES

CROSS-REFERENCE TO RELATED APPLICATIONS

This application is a continuation-in-part of U.S. patent application Ser. No. 12/308,409 which is a national phase entry in the U.S. of PCT/CA2007/001068 filed on Jun. 15, 2007 which claims priority from U.S. Patent Application 60/814,045 filed on Jun. 16, 2006 and 60/924,275 filed on May 7, 2007, the content of all of which is herewith incorporated in its entirety.

TECHNICAL FIELD OF THE INVENTION

The present invention relates to plant extracts which have been fermented with kefir grains, to methods of production of these extracts, as well as to the use of these fermented extracts in animal and human health.

DESCRIPTION OF PRIOR ART

Aromatic and medicinal plants have been and are presently important in the preventive and curative therapy of human and animal health. About 80% of the active substances used in occidental medicine come from plants.

From the traditional to the modern medicine, the evolution in the search for active principles originating from plants was carried out by phytochemical screening. First, the choice dealt with the whole plant, then certain parts of the plants (flowers, leaves, roots, barks . . . ) and subsequently with plant extracts (aqueous, alcoholic . . . ) and mixtures of active principles, and finally purified active principles. Today, these derivatives are usually obtained by hemisynthesis.

In ancient times, plants were used by instinct, empiricism according to religious or magical rituals. When analyzing and studying the therapeutic effects of plants, modern science has made it possible to specify, compare and classify their different properties to group the plants with similar effects, select the ones which are the most efficient and to make them known.

A vegetable is a source of molecules with therapeutic interest and vegetable screening has allowed to differentiate plants for bioactive compounds. The vegetables have the particularity of producing quite diversified natural substances. Besides primary metabolites (glucides, proteins, lipids, vitamins, minerals, etc.), the plants accumulate secondary metabolites (polyphenols, alkaloids, saponines, etc.) whose physiological and nutritional functions are not always obvious. In addition, these metabolites represent an important source of molecules which can be used by man or animal in the agri-food industry, in cosmetology and in pharmacology.

Plants produce a wide variety of secondary metabolites for their defense and their survival in the ecosystem. These secondary metabolites represent 1 to 3% of the dry plant. More than 100,000 substances have been identified and recognized for their biological activities as having a positive effect on health (anti-bacterial, anti-fungal, anti-viral, anticancer, anti-oxidant, cardioactive, etc.). These metabolites are presently used in the agri-food industry, in the cosmetic field and in the pharmaceutical field, and represent an income of about 10 billion dollars per year. Important metabolites as a source of nutritional or pharmaceutical active agents include phenolic compounds of vegetables: polyphenols and more particularly flavonoid. The flavonoids are present in a large number of plant varieties. For example, dried tea leaves contain up to 30% thereof. Flavonoids exist in the form of aglycones (genines) or in the form of glycosides. Flavonoids in the form of aglycones are known to have anti-bacterial, anti-inflammatory, anti-allergic, anti-mutagenic, anti-viral, anti-thrombotic, vasodilator activities. It is also known that the activity of flavonoids in the form of glycoside is less than in the form of aglycone. Flavonoids are divided in many classes of molecules of which the most important are the flavones, flavonols, flavanones, dihydroflavonols, isoflavones, isoflavanones, chalcones, aurones, anthocyanes and tannins. The flavonoids are widely present in aromatic, medicinal and edible plants, and also in fruits and vegetables.

Epidemiological studies have revealed that a regular consumption of fresh fruits and vegetables slows down the risk of developing cardiovascular diseases and the occurrence of certain forms of cancers. These effects are due, in part, to the relatively important concentrations of flavonoids which are present in these foods.

Flavonoids are also well known for their numerous biological activities, let us mention for example anti-allergic, anti-viral, anti-inflammatory and anticancer activities. These activities are in general considered to be due to their capacity to quench free radicals, to chelate metallic ions or to inhibit the enzymes that are responsible for the formation of free radicals such as hydroxyl (OH) and superoxide ($O^{2-}$) radicals.

Ever since the eighties, it is the discovery of the role of free radicals in pathological processes that has renewed the interest for these molecules of which the anti-oxidizing properties stand out to a large extent.

The mechanisms responsible for the action of an anti-oxidant may comprise: the direct quenching of the radicals, the inhibition of the enzymes and the chelation of the metallic traces which are responsible for the production of radicals, and the protection of the anti-oxidant defense systems.

Aglycone flavonoids inhibit enzymes such as α-amylase which plays an undesirable role in diabetes and obesity. Another example: xanthine oxydase is an enzyme which is involved in the gout disease. The aglycone flavonoids which have an effect on the activity of xanthine oxidase, may cause an improvement of the gout disease by simultaneously reducing the concentrations of uric acid and those of the superoxide radical in human tissues. These results have been confirmed by a study which has demonstrated the activity of about thirty aglycone flavonoids on the production of uric acid and the relationship between the chemical structure of the aglycone flavonoids and their activity as inhibitor of xanthine oxidase. Various aspects stand out from this study, among them the fact that glycosylated flavonoids possess much lower activities as compared to those of non glycosylated compounds. For example, rutine (glycoside) is nearly ten times less active than quercetine (aglycone). Other studies have shown that flavonoids are also good inhibitors of other enzymes which are responsible for the production of free radicals such as cyclooxygenase and lipooxygenase.

Presently, the properties of flavonoids are widely studied in the medical field where they are believed to possess anti-viral, anti-tumor, anti-inflammatory, anti-allergic and anti-cancer activities.

The anti-allergic effects of flavonoids are believed to be due to the influence of aglycone flavonoids on the production of histamine. Indeed, aglycone flavonoids inhibit enzymes, such as cyclic AMP phosphodiesterase and ATPase Ca2+-dependent, which are responsible for the release of histamine from mastocytes and basophiles. By inactivating this enzyme, quercetine (aglycone) has shown a higher potential of action than that of sodium cromoglycate used as medicament, by preventing the release of histamine and other endogenous substances which cause asthma.

The anti-inflammatory effects of flavonoids depend on the metabolism of arachidonic acid. Thus, under the action of cyclooxygenase and lipooxygenase, arachidonic acid is respectively metabolized into prostaglandins and leucotrienes, thereby being responsible for inflammatory phenomena. Some aglycone flavonoids are capable of modifying the metabolism of arachidonic acid in platelets and the effects of certain aglycones (quercetine, myricetine) are dose dependent. At high concentrations, they inhibit cyclooxygenase and lipooxygenase. However, at low concentrations, only lipooxygenase is affected. In addition, other aglycones such as apigenine and chrysine act mainly on the activity of cyclooxygenase.

The anti-ulcerative effects of flavonoids have also managed to be put forward. In experiments carried out on rats, it was established that aglycones (quercetine and naringenine) play an important part in the reduction of ulcer and the protection of gastric cells. Other studies have made it possible to establish a close relation between the anti-ulcerative properties of quercetine, naringenine, rutine and kaempferol, and the production of PAF (Platelet Activating Factor) which is a potential ulcerogenous agent. Indeed, it has appeared that the reduction of gastro-intestinal damages is probably due to the inhibition of PAF by means of these aglycone flavonoids.

Finally, the anti-cancer effects of flavonoids are constantly cited in the literature and in particular these effects are present practically in all types of tea, catachine has shown an anti-cancer activity.

Glycoside flavonoids can be extracted with water in a form that is not very active since they are soluble. They should however be deglycosylated to make them active in free form (aglycone). The glycosylated flavonoids have much lower activities than those of non glycosylated compounds.

Flavonoids are polyphenols, they can be ingested with food pigments (fruits, vegetables, plants, etc.) or as supplement. Their bioavailability depends on the intestinal absorption which is defined by their chemical composition. The vast majority of phenolic glycosides are present in the vegetable cells in combined form O- or C-glycosylated. Bound sugar may be mono-, di- or polysaccharide. Glycosylation increases the solubility of aglycones in water, increases their mobility and facilitates their transport in the plant.

A study shows that the phenolic compounds present in vegetables are absorbed by the ileum through active transport and are therefore saturable (glycosides), and after deglycosylation with the lactase phlorizine hydrolase (aglycone).

To release the active agent, it is important that the glycoside be hydrolyzed through acid and/or enzymatic means. Deglycosylation of flavonoids is an essential factor which has an influence on the beneficial potential of the components of the plant. Thus, the flavonoids which are polyphenols from the secondary metabolism of the plant constitute the more important group of natural phenols. They have a high anti-oxidizing, anti-inflammatory, anti-allergic, anti-bacterial and anti-viral capacity through their aglycone molecule and this biological activity represents a beneficial potential for health.

The small intestine is therefore the main absorption site for many glycosylated flavonoids. Thus, the phenolic compounds of an aqueous infusion are mainly in glycosylated form. When they reach the stomach, gastric acidity is responsible for deglycosylation onset by transforming for example polymeric flavonol units into oligomeric flavonol units. The glycosylated oligomers are transported towards the epithelial cells of the intestinal mucosa (enterocytes) and are hydrolyzed through enzymatic means by the lactase phlorizine hydrolase (LPH) into aglycones and free sugars (glucose, galactose, maltose, etc.). The aglycones are absorbed by passive transport in the region of the brush type border of the enterocytes of the ileum. The glycosides which have not been deglycosylated are absorbed (a minority) by active transport (sodium pump) but a majority goes into the colon where the colic bacteria (bifidobacteria, *lactobacillus*, bacteroids) deglycosylate them enzymatically (glycohydrolases) and release the aglycone. A portion of the aglycones are reabsorbed and another portion is oxidized.

The intestinal microflora plays a major part in the pharmacological action of medicinal plants. The enzymatic activity of the intestinal bacteria releases the active agents by deglycosylation and this activity varies depending on the individuals and their state of health.

It has already been shown that it is possible to deglycosylate glycoside flavonoids in an aqueous solution. Water soluble glycoside flavonoids comprise aromatic mono-, di- or trisaccharide compounds. They are precursors of aromas and of flavors. For instance, glycosides extracted from hop, by enzymatic hydrolysis (fermentation with yeasts) and then by acid hydrolysis, will release the aglycone to give malt flavor to beer.

In another instance, the preparation of a fermented drink based on water, sugar (2.5 to 3.5%) and aromas (3 to 5%), where the proportion of kefir grains (GK) is 10-30% is obtained. The drink is fermented at a temperature of 20-25° C. during 48-72 h. This thirst-quenching drink is called: water kefir.

A process for the preparation of a fermented drink from an aqueous extract of tea or coffee (0.5 to 2%) with sugar (4 to 13%) and fermented with at least one yeast strain (*Saccharomyces cerevisiae*) and a bacterial strain (*Acetobacter* or *Glucunobacter*) in one or more steps. Fermentation is carried out at 27-32° C. and does not exceed 24 h. Finally, the product is heated at 85-140° C. during 15 to 30 mn. (CA2197481 published on the 14 Aug. 1997).

Reiss describes a process for the preparation of fermented drinks from fermented black tea, in a single step, with a yeast strain (*Schizosaccharomyces pombe*) and a bacterium strain (*Acetobacter xylinum*) during 6 days. (Reiss J The tea fungus and its metabolic products. Deutsche lebensmittel-Rundschau, 83, 286-290, 1987).

Patent Application publication US2003147980 (published on the 7 Aug. 2003) shows that soluble plant flavonoids are glycosylated flavonoids. It provides a method for the production of aglycone enriched flavonoid extract from a starting product containing an appropriate and/or conjugated glycoside flavonoid including the following steps: acid or enzymatic hydrolysis to convert the glycoside or the conjugated flavonoid into an aglycone flavonoid; adjustment of the pH (alkaline pH higher than 8.5) to solubilize the aglycone flavonoid and to remove the insoluble part; and a second pH adjustment (acid pH from 2 to 6) to make the soluble aglycone flavonoid relatively insoluble and to provide an extract containing the same thing. A study on the fermentation of the juice of soya bean with kefir cultures and supplemented with extracts of *Rhodiola* has demonstrated that the content of bound phenolic compounds (salidroside) is decreased and that the free phenolic compounds are increased (tyrosol). The result is an inhibition of α-amylase, an increase of Angiotensin 1-Converting Enzyme (ACE) but also of the anti-oxidizing activity. The product may be used in therapies for postprandial hyperglycemia (diabetes) (Kwon, Y-I. et al., Anti-Diabetes functionality of Kefir culture-mediated fermented soymilk supplemented with *Rhodiola* extracts. Food Biotechnology, (2006) 20:13-29). Patent Application Publication US2003/0185811 (Teasdale et al.) provides a process for extracting active ingredients from plants which increases the bioavailability of these active ingredients. Patent Application EP 1279727 provides a process for the bioconversion and biotransformation of natural medicines. An aqueous extract, more often hydro-alcoholic, sterilized and whose pH is adjusted (pH 6.8), is inoculated with intestinal probiotics in a complex culture medium (growth medium containing sugars, proteins, vitamins, minerals, yeast extracts). The fermentation temperature is 37° C. for a period of 6-8 h or 18-24 h and under anaerobiosis (without oxygen). The probiotic bacteria are traditionally used in extraction processes from plants to generate a fermentation of the plant extracts. More often, the temperature is thermophilic (higher than 30° C.). The bioavailability of the active compounds of the plants is critical to obtain a maximum beneficial effect.

Even if modern medicine is well developed in most of the world, large sections of the population, in the developing countries, depend today on professionals who use traditional medicine and medicaments based on plants, as the primary intent.

In the past recent years, public interest for natural therapies has considerably increased in the industrial countries and the use of plants is expanding.

It would therefore be desirable to obtain compositions comprising polyphenols (such as flavonoids), in an active form (such as in the form of aglycone). These compositions would be quite useful in various aspects of animal and human health. It would also be desirable to obtain methods for producing such compositions.

BRIEF DESCRIPTION OF THE INVENTION

The invention concerns compositions comprising an extract of plants which have been fermented with a kefir grain.

More particularly, an aspect of the invention concerns a method for the production of a fermented plant extract. The method comprises fermentation of a plant extract by means of a kefir grain in order to give a fermented plant extract. Broadly, the method comprises (i) providing a fermentable aqueous plant medium consisting of an aqueous plant extract, a fermentable carbohydrate source and a kefir grain, and (ii) incubating the fermentable aqueous plant medium under conditions to favor the conversion of the fermentable carbohydrate source to acetic acid to provide the fermented plant extract. In a variant of the invention, the plant extract is an aqueous extract. In a variant of the invention, fermentation is carried out by complying with at least one of the following criteria: a duration of fermentation between 20 and 60 days; a static fermentation; a fermentation temperature lower than 30° C.; a batch fermentation; a fermentation at pH<4 and Brix<4; a fermentation followed by a drying step. In an embodiment, the acqueous plant extract is from an extract selected from the group consisting of an agrimony extract, an alfalfa extract, an anise extract, an annato seed extract, an artichoke extract, an ashwagandha extract, an astragalus extract, a basil extract, a birch extract, a black pepper extract, a blackberry extract, a burdock extract, a celery extract, a chamomile extract, a cinnamon extract, a clove extract, a coffee extract, a coriander extract, a cumin extract, a dandelion extract, a desmodium extract, an elder flower extract, a eucalyptus extract, a euphrasia extract, a fennel extract, a garlic extract, a ginger extract, a ginseng extract, a green tea extract, a hibiscus extract, a holy basil extract, a hop extract, a lapacho extract, a lavender extract, a lemongrass extract, a maca extract, a matcha tea extract, a meadowsweet extract, a milk thistle extract, a neem extract, a nettle extract, a parsley extract, a passionflower extract, a peppermint extract, a plantain extract, a raspberry extract, a *rhodiola* extract, a rooibos extract, a rosemary extract, a sage extract, a savory extract, a turmeric extract, a valerian extract, a violet leaf extract, a wheat grass extract, a white willow extract, a yarrow extract, a yerba mate extract, a lemonbalm extract, a puncture vine extract, a ginkgo extract, a saw palmetto extract, a Saint-John's wort extract, a cayenne extract, a spirulina extract, a kava kava extract, a kelp extract, a feverfew extract, a barley extract, an alfalfa extract, a licorice extract and combinations thereof.

According to another aspect, the invention concerns a fermented plant extract obtained by the method described herein.

According to another aspect, the invention concerns a fermented plant extract comprising a high amount of a deglycosylated active principle and a fermentation product of a kefir grain. In a variant of the invention, the active principle is partially or completely deglycosylated. According to another aspect of the invention, the fermented plant extract is derived from an aqueous plant extract. According to another variant of the invention, the fermented plant extract is derived from an extract selected from the group comprising a thyme extract, an oregano extract, an extract of *Echinacea* (purple coneflower), a black tea extract, a tansy extract and a valerian extract.

According to another aspect, the invention concerns a powder comprising a product of milk or vegetable origin, and the fermented plant extract according to the invention. In a variant of the invention, the powder may be obtained by drying a support comprising the product of milk or of vegetable origin. In a variant of the invention, the product of milk origin is selected from milk, whey, buttermilk and ultra-filtrate. In a variant of the invention, the milk may be whole, half skimmed or skimmed. In a variant of the invention, the product of vegetable origin is selected from cereals, high protein vegetables and oleaginous vegetables. In a variant of the invention, the cereals include wheat, barley, oat, corn, sorghum. In a variant of the invention, the high protein vegetables include lupine, peas. In a variant of the invention, the oleaginous vegetables include soy, sunflower and canola. In another variant of the invention, the support is selected from whey, buttermilk, ultra-filtrate, wheat, barley, oat, corn, lupine, pea, soy, sunflower and canola.

According to another aspect, the invention concerns a composition comprising a plant extract which has been fermented with a kefir grain and an excipient. According to another variant, the invention concerns a composition comprising a plant extract which has been fermented by the method described herein.

According to another aspect, the invention concerns a use of the plant extract which has been fermented by the method described in the present disclosure, as an antiseptic. In another variant of the invention, the fermented plant extract is used to manufacture an antiseptic medicament. In another variant of the invention, the fermented plant extract is an extract of thyme and an extract of oregano.

According to another aspect, the invention concerns a use of the plant extract which has been fermented by the method described in the present disclosure, as an antitussive. In another variant of the invention, the fermented plant extract is used to manufacture an antitussive medicament. In another variant of the invention, the fermented plant extract is an extract of *echinacea*.

According to another aspect, the invention concerns a use of the plant extract which has been fermented by the method described in the present disclosure, as liver detoxifier. In another variant of the invention, the fermented plant extract is used for the manufacture of a medicament for the detoxification of liver. In another variant of the invention, the fermented plant extract is an extract of black tea.

According to another aspect, the invention concerns a use of the plant extract which has been fermented by the method described in the present disclosure, as anti-migraine drug. In another variant of the invention, the fermented plant extract is used to manufacture an anti-migraine medicament. In another variant of the invention, the fermented plant extract is an extract of tansy.

According to another aspect, the invention concerns a use of the plant extract which has been fermented by the method described in the present disclosure, as an anti-stress. In another variant of the invention, the fermented plant extract is used to manufacture an anti-stress medicament. In another variant of the invention, the fermented plant extract is an extract of valerian.

According to another aspect, the invention concerns a use of the plant extract which has been fermented by the method described in the present disclosure, to improve intestinal hygiene. In another variant of the invention, the fermented plant extract is used to manufacture a medicament for improving intestinal hygiene. In another variant of the invention, the fermented plant extract is an extract of oregano and an extract of black tea.

According to another aspect, the invention concerns a use of the plant extract which has been fermented by the method described in the present disclosure, to provide a food supplement. In another variant of the invention, the fermented plant extract is used to manufacture a medicament for providing a food supplement. In another variant of the invention, the fermented plant extract is an extract of thyme and an extract of oregano.

According to another aspect, the invention concerns a use of the plant extract which has been fermented by the method described in the present disclosure to stabilize a product and increase its storage time. In another variant of the invention, the fermented plant extract is an extract of thyme and an extract of oregano.

According to another aspect, the invention concerns a use of the plant extract which has been fermented by the method described in the present disclosure to improve animal yield. In another variant of the invention, the fermented plant extract is used to manufacture a medicament for improving animal yield. In another variant of the invention, the fermented plant extract is an extract of thyme and an extract of oregano. In another variant of the invention, the plant extract is in the form of a powder.

According to another aspect, the invention concerns a method for treating an infection comprising administering the plant extract as fermented by the method described in the present disclosure in order to reduce the infection. In a variant of the invention, the infection is caused by a bacterium. In a variant of the invention, the fermented plant extract is an extract of thyme and an extract of oregano.

According to another aspect, the invention concerns a method for treating cough comprising administering a plant extract as fermented by the method described in the present disclosure in order to reduce cough. In a variant of the invention, the fermented plant extract is an extract of *echinacea*.

According to another aspect, the invention concerns a method for the detoxification of liver comprising administering a plant extract as fermented by the method described in the present disclosure, as a liver detoxifier. In a variant of the invention, the fermented plant extract is an extract of black tea.

According to another aspect, the invention concerns a method for treating migraine comprising administering a plant extract as fermented by the method described in the present disclosure, as an anti-migraine agent. In a variant of the invention, the fermented plant extract is an extract of tansy.

According to another aspect, the invention concerns a method of treatment for decreasing stress comprising administering a plant extract as fermented by the method described in the present disclosure, as an anti-stress agent. In a variant of the invention, the fermented plant extract is an extract of valerian.

According to another aspect, the invention concerns a method of treatment for improving intestinal hygiene, comprising administering a plant extract as fermented by the method described in the present disclosure to improve intestinal hygiene. In a variant of the invention, the fermented plant extract is an extract of oregano and an extract of black tea.

According to another aspect, the invention concerns a method of treatment for improving an animal's diet comprising administering a plant extract as fermented by the method described in the present disclosure to provide a dietary supplement. In a variant of the invention, the fermented plant extract is an extract of oregano and an extract of black tea.

According to another aspect, the invention concerns a method for stabilizing a product and increasing its storage time, comprising adding a plant extract as fermented by the method described in the present disclosure to stabilize the product and increase its storage time. In a variant of the invention, the fermented plant extract is an extract of oregano and an extract of black tea.

According to another aspect, the invention concerns a method for improving animal yield comprising administering a plant extract as fermented by the method described in the present disclosure to improve animal yield. In a variant of the invention, the fermented plant extract is an extract of oregano and an extract of black tea.

According to another aspect, the invention concerns a method of treatment comprising administering a powder described in the present disclosure to provide a food supplement.

BRIEF DESCRIPTION OF THE FIGURES

Having thus generally described the nature of the invention, reference will now be made to the accompanying drawings, showing by way of illustration, a preferred embodiment thereof, and in which:

FIG. 7 shows a comparison of the aromatic profile of an aqueous extract of non fermented *Thymus vulgaris* (EAT), and an aqueous extract of kefirated *Thymus vulgaris* (EATK).

FIG. 8 shows a comparison of the aromatic profile of an aqueous extract of non fermented *Valerian officinalis* (EAV), and an aqueous extract of kefirated *Valerian officinalis* (EATK).

FIG. 9 shows the antibacterial effect of an extract of kefirated *Thymus vulgaris* on the growth of a plurality of bacterial strains. Aqueous extract of thyme (EAT), essential oil from thyme (HET) and kefirated thyme extract (EAKT).

DESCRIPTION OF THE VARIANTS OF THE INVENTION

Figure 1:
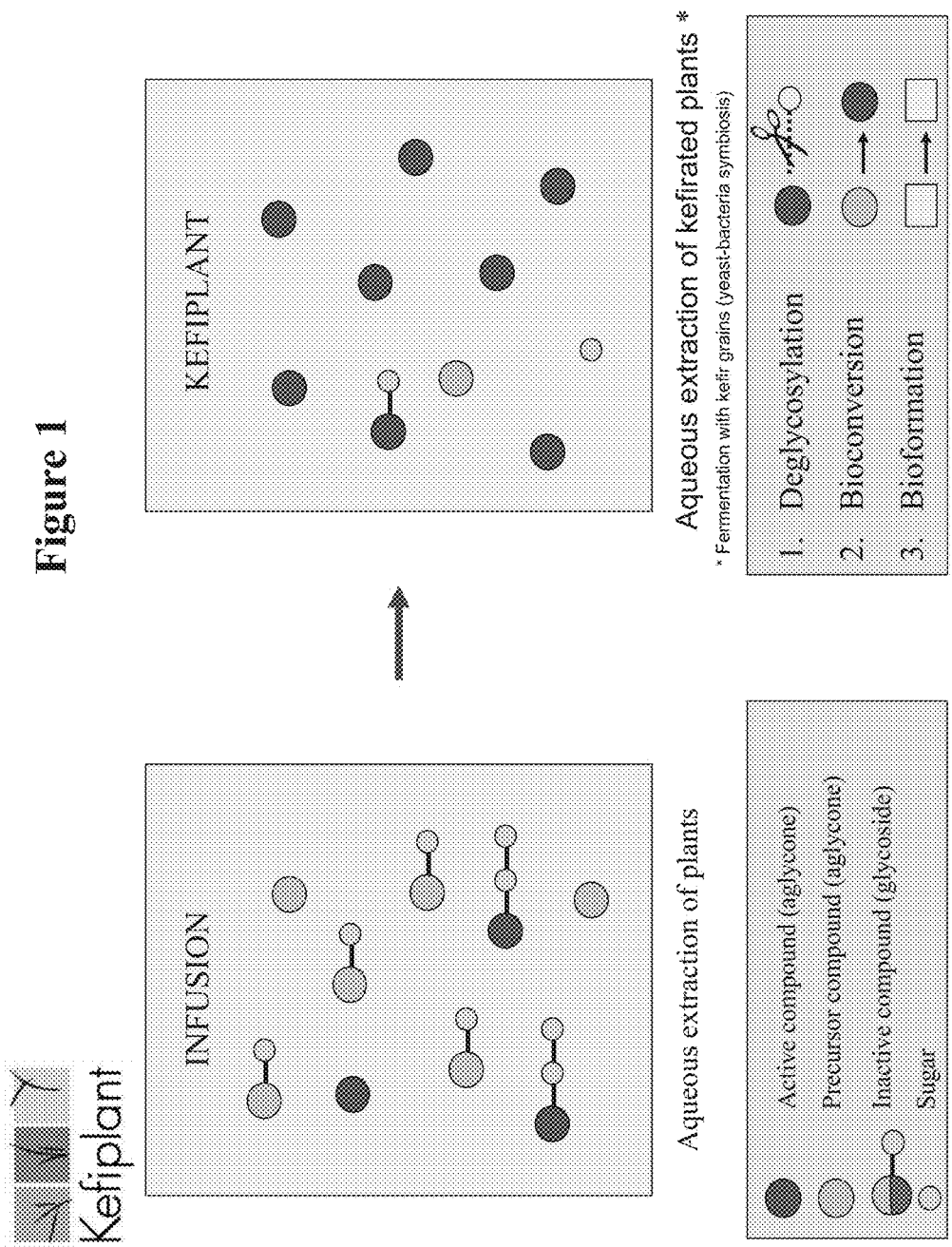
FIG. 1 shows the proposed mechanism for kefication.
Figure 2:
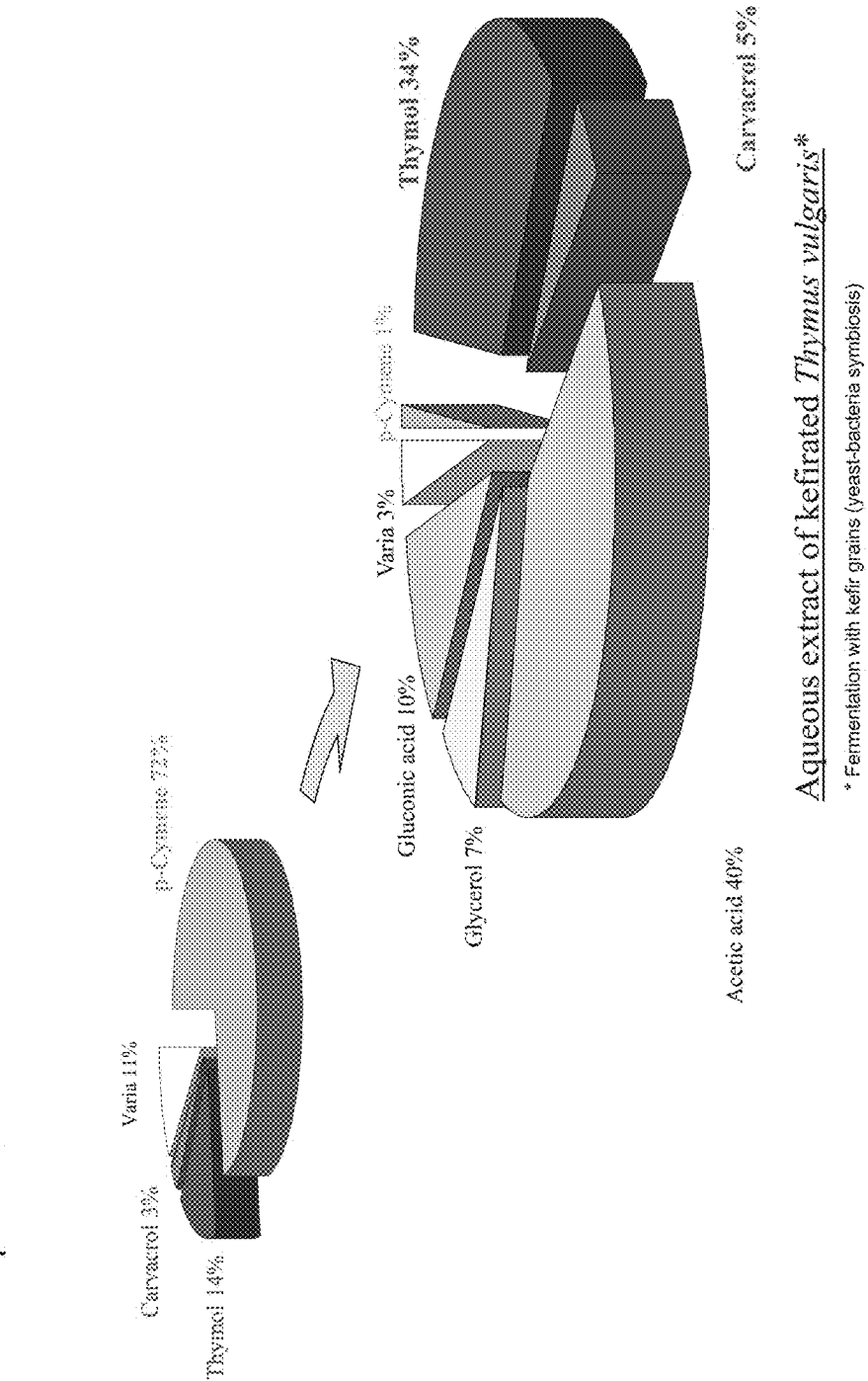
FIG. 2 shows the effect of kefication on the components of a non fermented extract of *Thymus vulgaris* (at the top on the right) and as kefirated (at the bottom on the left).

The aqueous plant extract allows to recover phenolic compounds from the vegetables which have a biological activity for health. However, generally, these compounds are essentially in glycosylated form and therefore possess very little activity. Activation of the glycosides takes place at the level of the enterocytes of the intestinal mucosa and in particular at the level of the brush border of the intestinal villosities. Glycohydrolases release the active aglycone that will be absorbed in the blood stream. The glycosides which reach the colon may release the aglycone that will be absorbed in the same manner as water, by the colon mucosa, and then transported to the liver.

Thus, individuals with eroded intestinal villosities for physiological reasons (weaning period of new born babies, aging), pathological reasons (Crohn's disease, allergies, auto-immune diseases) or for medical reasons (anti-cancer, antibiotic, anti-inflammatory treatment) or for psychological reasons (stress, fatigue, anxiety) cannot absorb glycosylated flavonoids because their brush border is deficient and the fact that no more enzymes (glycol-hydrolases) are present.

A plant extract which is fermented with a kefir grain may permit the release in situ of aglycone flavonoids and therefore the intestinal absorption will be facilitated even in the cases previously described. On the other hand, certain precursors which are deglycosylated by acid hydrolysis and the α-glucosidases of the microorganisms of the kefir grain will be converted into active agents (bioconversion).

Kefir is a fermented milk or fruit drink whose original feature is the use of a specific ferment: kefir grain. Kefir grain (GK) is a natural biological entity which is obtained through the symbiosis of yeasts and bacteria "GRAS" (Generally Recognized as Safe) and which is trapped in an insoluble polysaccharide matrix. It allows for a continuous fermentation of food and vegetable products without specific addition of activator. One may distinguish between milk GK (opaque) and fruit GK (translucent). The GK's that are used must not contain pathogen germs (coliform bacteria, staphylococci, *Salmonella, Listeria*, etc.) and must conform to the law in force for the manufacture of kefir (international dairy federation norm (FIL) 163/1992). Generally, GK's are used for the production of leavens which will be used for the fermentation of food supplements (EP 0498506) or drinks.

Growth in a non renewable medium, or batch growth, does not allow bacteria (such as pure cultures) to grow indefinitely and they stop after 24 h to 48 h of fermentation through exhaustion of the substrate, accumulation of toxic products and increase of the acidity.

Contrary to pure bacterial cultures, GK is resistant to acidity (pH lower than 2). In contrast to pure strains which first use sugar to mainly produce acids, GK uses sugar to produce acids and also polysaccharides which constitute an envelope for the GK. Thus, during fermentation with a GK, the quantity of the latter increases from 30 to 40%. In a batch culture, GK can therefore ferment for a longer period of time than pure strains and produce more intense modifications of the components of the substrate (bioconversion).

An increase in the number of bacteria or yeasts is a discontinuous phenomenon while an increase of the biomass is a continuous phenomenon which is dependent on fermentation time. Mixed strains develop asynchronously and their viability is limited in time. It is necessary to balance again the substrate or to seed again the strains to revive fermentation. GK is made of strains in symbiosis and the development is synchronous, which means that it is time viable up to more than 60 days. Inoculation is continuous due to the fact that the production of polysaccharide again traps microorganisms which inoculate again the fermentation medium. The more the GK strain multiplies, the longer the fermentation is.

Pure strains are exhausted after 24 h, while GK keeps on fermenting even after 30 days.

The method of production described in the present disclosure may be applied to different aromatic, medicinal or dietary plants (such as fruits and vegetables). The plants which are chosen may also be selected according to their geographical origin. The method may be applied to the plant as a whole or to part of the plant. When part of a plant is chosen, above ground parts (flowers, leaves, barks, seeds, fruits), underground parts (roots, rhizomes, tubers), juices originating from the plants (or part of the plants) or a combination thereof may be chosen. The plants used may be fresh or dried.

In the methods and fermented products described herein, it is possible to use various aqueous plant extracts, such as, for example, an agrimony extract, an alfalfa extract, an anise extract, an annato seed extract, an artichoke extract, an ashwagandha extract, an astragalus extract, a basil extract, a birch extract, a black pepper extract, a blackberry extract, a burdock extract, a celery extract, a chamomile extract, a cinnamon extract, a clove extract, a coffee extract, a coriander extract, a cumin extract, a dandelion extract, a desmodium extract, an elder flower extract, a eucalyptus extract, a euphrasia extract, a fennel extract, a garlic extract, a ginger extract, a ginseng extract, a green tea extract, a hibiscus extract, a holy basil extract, a hop extract, a lapacho extract, a lavender extract, a lemongrass extract, a maca extract, a matcha tea extract, a meadowsweet extract, a milk thistle extract, a neem extract, a nettle extract, a parsley extract, a passionflower extract, a peppermint extract, a plantain extract, a raspberry extract, a *rhodiola* extract, a rooibos extract, a rosemary extract, a sage extract, a savory extract, a turmeric extract, a valerian extract, a violet leaf extract, a wheat grass extract, a white willow extract, a yarrow extract, a yerba mate extract, a lemonbalm extract, a puncture vine extract, a ginkgo extract, a saw palmetto extract, a Saint-John's wort extract, a cayenne extract, a spirulina extract, a kava kava extract, a kelp extract, a feverfew extract, a barley extract, an alfalfa extract and/or a licorice extract.

Plant extracts used may be aqueous solutions prepared from powders or plant pieces. These aqueous extracts are prepared under hot or cold conditions by infusion, decoction, percolation or maceration. When infusion is used, the aqueous extract (EA) may be obtained from 10 to 50 g/L of the dried plant in water. Water temperature may be between 50-90° C. and the infusion may last for 20 to 60 minutes. The aqueous extract may then be filtered to separate the insoluble particles from the soluble particles.

The plant extract is then treated by fermentation by means of a kefir grain. The kefir grain may be supplied by the Symbiotec laboratory, it consists of a symbiosis of yeasts and GRAS bacteria. Before starting the fermentation, 60-80 g/L of sugar (saccharose, glucose, honey or a combination thereof) can be combined with the aqueous extract. Addition of sugar may be carried out by stirring the aqueous extract. The mixture may then be cooled between about 25 and 29° C. To start the fermentation, an inoculum of kefir grains is added. This inoculum varies depending on the quantity of aqueous extract. According to a variant of the invention, this inoculum varies between about 10 to 30 g/L. The fermentation lasts about 20 to 60 days. The fermentation is a mesophilic fermentation, the fermentation temperature can therefore vary between 24-28° C. Fermentation may also take place under static conditions, i.e. where no stirring takes place during fermentation. It is possible that samplings be made during fermentation to make sure that the quality of the fermentation is maintained. When the fermentation is over, the fermented extract may be filtered by means of a filter (plate or cartridge) with pores of 45 μm or 0.2 μm. As an alternative, the extract may be centrifuged at about 2000-5000 tr/mn during 10 to 20 mn. For purposes of analysis, the aqueous extracts and fermented aqueous extracts may be kept at −20° C. The control is a non-fermented aqueous extract.

Without being limited to theoretical conclusions, the fermentation of aqueous plant extracts by means of kefir grains allows to hydrolyze (by an acid hydrolysis combined with an enzymatic hydrolysis that can take place simultaneously) glycosylated flavonoids, which are not much active (FIG. 1). The acid hydrolysis is due to the conversion of sugar into acetic acid and the enzymatic hydrolysis is due to the enzymes (glycohydrolases) produced by the GK. This procedure naturally enriches the aqueous extract with active aglycone flavonoids.

Some aglycone flavonoids released are natural precursors of other more active aglycone flavonoids than their precursor. For example: an extract of willow bark (*Salix fragilis*) provides a glycoside, namely saliciline, which, after acid hydrolysis (chemically) releases the aglycone which is a precursor of salicylic acid, which is the basis of aspirin. During fermentation with the kefir grain, the same phenomenon takes place, however through the biological route. Precursors of terpenes (such as: para-cymene) whose activity is low, are also converted into their terpene homologues which are much more active (such as: thymol, carvacrol). The production of organic fatty acids, of glycerol, of short chain fatty acids and of ethanol also seems to have a synergic role with the aglycone flavonoids.

Tisanes (aqueous extract) also called herbal teas, constitute a means of first intent to prevent certain pathological health problems. A tisane is not solely a water input. It is a medicinal preparation which is useful in medicine and in phytotherapy. It must meet certain criteria to be of good quality: the quality of the plant, the time of infusion, the conditions of use and the correction for taste. The content of active principle varies depending on many factors which determine its efficiency. So, when one proceeds to analyzing a tisane, it is noted that a number of active ingredients are in glycosylated forms. Thus, 70 to 80% of the phenolic compounds present in vegetables (CPV) are soluble in water, and this is also the case for all the tisanes (aqueous extract) prepared by infusion, decoction, maceration or percolation of plants which contain CPV which more often are glycosylated (increase solubility). 80-90% are glycosides (very little active) and 10 to 20% are aglycones (active), which explains certain random effects of the plant infusions used in phytotherapy. A large number of biologically active compounds are glycosides (hormones, edulcorants, alkaloids, flavonoids, antibiotics, saponines, etc.) which are water soluble. A plant produces glycoside polyphenols which are important compounds in traditional medicine. Many glycosylated flavonoids are prepared by biosynthesis or by biotransformation for pharmaceutical use.

The expression "high content" of deglycosylated active principle corresponds to a value higher than 90%. The expression "partly deglycosylated" corresponds to a glycosylation lower than 50%. The expression "completely deglycosylated" means that all the glycoside flavonoids (di- and polysaccharide) have been deglycosylated.

When a tisane is absorbed, activation of the active agents takes place at the intestinal level in three phases. A first phase, at the level of the stomach where the acidity will start to deglycosylate glycoside flavonoids (di- and polysaccharide) but releases only very little aglycone flavonoids. Deglycosylation is lower than 50%. A second phase, at the level of the small intestine, where the glycohydrolases of the epithelial cells of the villosities will release aglycone flavonoids (mono-saccharide), by enzymatic action. If the aglycone is an active agent, it is efficient but if it is a precursor, its action is limited. A third phase, at the level of the colon, where the glycosidases of the colic flora will release aglycone flavonoids also by enzymatic action. A kefirated tisane (e.g. fermented with kefir grains) restores the three preceding phases, however before absorption, so when they are absorbed, the components are directly assimilated. Deglycosylation is normally higher than 90%. Acidifying of the tisane with kefir grains will make it possible to deglycosylate the glycoside flavonoids (di- and polysaccharide) and at the same time the glycohydrolases of the kefir grain will release aglycone flavonoids from the glycoside flavonoids (mono-saccharide). Bioavailability of the flavonoids is increased. Aglycone is either an active agent (e.g. thymol) or a precursor of active agent whose activity is limited (e.g. para-cymene).

Kefication is defined as subjecting an aqueous plant extract to fermentation with kefir grains. With respect to the aqueous plant extract which is subject to kefication, it is said that it is "kefirated". Kefication is controlled by means of parameters, such as pH and Brix. The pH is used to measure the amount of free protons ($H^+$) in a solution through a pH-meter or any other method known by one skilled in the art. Brix is used to determine the portion of sugar in a liquid through, for example, a refractometer (or aerometer). When the parameters are in accordance with the anticipated standards (for example, pH<4 and Bris<4), kefication is stopped in order that the mixture be thereafter filtered.

Fermentation is carried out by complying with at least one of the following criterions: a fermentation which lasts between 20 and 60 days; a static fermentation; a fermentation temperature lower than 30° C.; a batch fermentation; a fermentation at pH<4 and Brix<4; the fermentation is followed by a drying step. A static fermentation takes place when no stirring takes place during fermentation. Batch fermentation takes place when the fermentation is discontinuous.

Kefication converts the precursor into an active agent (bioconversion) and thus increases the amount of active agents. Kefication is responsible for the bioformation of active agents such as organic acids (acetic, gluconic, succinic acids). Thus when a kefirated tisane is absorbed, the active agents are directly available in a single phase. Bioavailability of the components of a kefirated tisane is much higher than that of a standard tisane. The anti-oxidizing effect brought about by the aglycone flavonoids of kefirated tisanes is also much higher that the one brought about by the glycoside flavonoids of standard tisanes.

Figure 3:
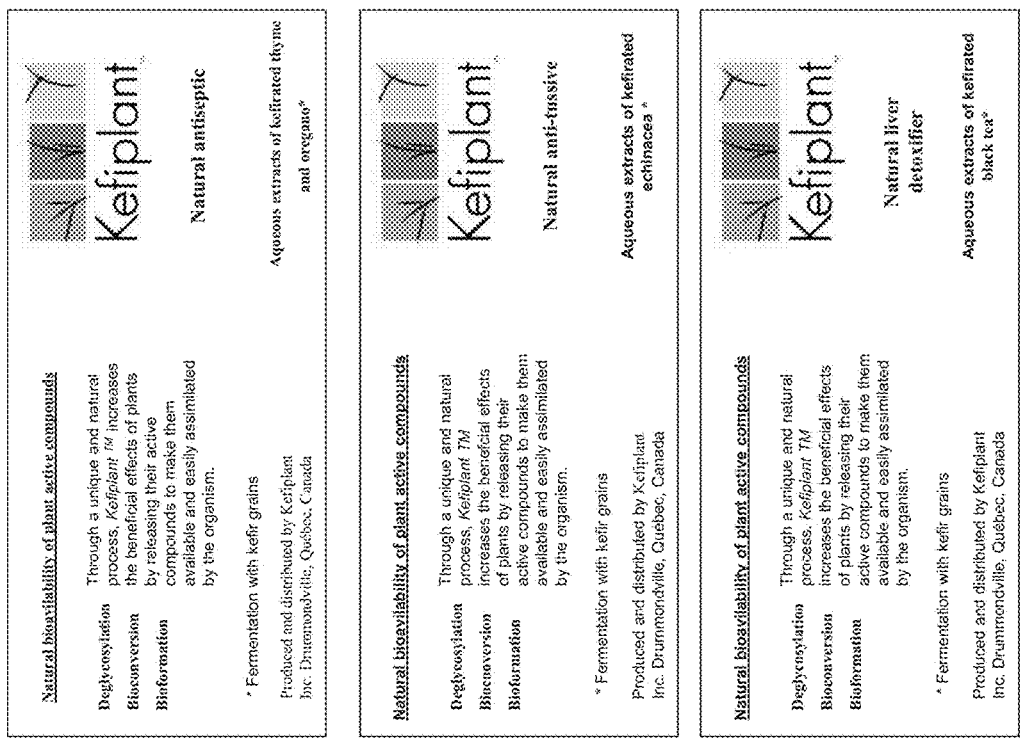
FIG. 3 shows proposed uses of kefirated plant extracts from thyme and oregano, *echinacea* and black tea.
Figure 4:
FIG. 4 shows proposed uses of kefirated plant extracts from tansy, valerian, thyme, oregano and black tea.

Fermented or kefirated compositions may have many uses: antiseptic (such as antibacterial), antitussive, liver detoxifier, anti-migraine, anti-stress, improvement of intestinal hygiene. Some examples are presented in FIGS. 3 and 4. For example, kefirated aqueous thyme and oregano extracts may be used as natural antiseptic. Kefirated aqueous *echinacea* extracts may be used as natural antitussive. Kefirated aqueous black tea extracts may be used as natural liver detoxifier. Kefirated aqueous tansy extracts may be used as natural anti-migraine. Kefirated aqueous valerian extracts may be used as natural anti-stress. Kefirated aqueous oregano extracts may be used for intestinal hygiene. Intestinal hygiene includes all conditions related to the health and the function of the intestine such as intestinal microflora, intestinal transit and/or intestinal absorption.

Fermented or kefirated compositions may have other uses, such as for improving the animal yield, for providing a food supplement, for improving zootechnical performances of rented animals, for stabilizing a product and increasing its storage time. Improvement of the animal yield may be determined, for example, by a decrease of the death rate in the animals, an increase of food consumption by the animals, an increase of the average daily gain (GMQ), a decrease of the consumption index (IC), an increase of the weight of the carcass of the animals, and/or an increase of the average weight at the end.

Fermented plant extracts and fermented kefirated compositions may, also, be in the form of a powder which is obtained by drying on a suitable support. A powder is a dehydrated substance, and it may even be dried, solid and divided into very fine particles. The powder obtained has a particle size between 1 and 100 microns, and preferably between 5 and 50 microns. The particle size may be determined by a laser granulometer of the type MALVERN™. The advantage of this presentation allows for its incorporation into food preparations or to directly obtain a complete food. It also makes it possible to stabilize the product and to increase its storage time.

The supports may consist of foods that are used for feeding living beings, such as animals and human beings. The animals may be mammals such as bovine, porcine, ovine or equine species. They may also be fishes or poultry as well as pets, such as dogs and cats.

The supports may consist of products of milk origin (such as inter alia: milk, whole milk, half skimmed milk, skimmed milk, whey, buttermilk, ultra-filtrate), or of vegetable origin: cereals (such as inter alia wheat, corn, barley, oat, sorghum), proteinaceous plants (such as inter alia lupine, peas), oleaginous plants (such as inter alia soy, sunflower, canola).

In order to dry or dehydrate the fermented or kefirated compositions, they are introduced into a tank containing, for example, whey (from 28 to 35% of dry matter) at the rate of 5 to 10% (v/v). The mixture thus obtained is concentrated with 50 to 60% of dry matter. After crystallization, the composition that is obtained is dried in a spray tower ("spray drying").

The powder thus obtained may advantageously be incorporated into food preparations at the rate of 10 to 20% (p/p) or may constitute the food ready for use.

The properties of this fermented or kefirated composition in powder form are comparable to those obtained with liquid fermented or kefirated compositions.

Example I—Analysis of the Aromatic Profiles

For the purpose of analyzing the aromatic profiles of the fermented extracts, three types of extracts may be prepared for the purpose of analyzing them by chromatography in gaseous phase combined with mass spectrometry (CPG-SM):

1. Extracts obtained by hydrodistillation of plants: vegetable starting material, 500 mL water, duration of hydrodistillation: 8 hours. The quantity of vegetable starting material used varies depending on the nature of the plant. Example: thyme: 7.86 g of vegetable matter, essential oil obtained: 0.19 g. Extraction yield: 1.07 g.
2. SDE extract (Simultaneous Extraction/Distillation) of the type Lickens & Nickerson of plant infusions: extraction protocol: 500 mL of infusion, 30 mL of pentane (flask)+ 15 mL in the loop, 2 hours of extraction, recovery of the extraction solvent and mild evaporation under nitrogen flow up to 2 mL—keeping samples at −20° C. until analysis.
3. SPME extracts (Solid Phase Microextraction) of plant infusions. The SPME fiber which has been selected for this extraction is an absorbing fiber of the type polydimethylsiloxane (PDMS) 100 μm. The fiber is directly immersed into the infusion under magnetic stirring during 1 hour at room temperature (air conditioned room at 21° C.). The fiber is then directly injected into the injector of the chromatograph (specific insert and septum for SPME).

Example II—CPG-SM Analyses

In order to analyze the fermented extracts, CPG-SM analyses may also be carried out. The chromatographic conditions must first be optimized for each type of plant infusion and each type of extract. However, in a general manner, the analyses may be carried out on an Agilent column J&W, DB5-MS (5% phenylmethylsiloxane), 30 m long×250 μm internal diameter×1 μm film thickness. The analyses are carried out under a constant flow of helium: 1.4 mL/min (average speed of 30 cm/sec). The temperatures of the injector and of the detector (transfer line) are kept at 290° C. for the analyses of liquid extracts. For the SPME extracts, the temperature of the injector is 250° C. (desorption temperature of the volatile compounds of the PDMS fiber). The mode of injection depends on the type of extract that is analyzed. For the Lickens & Nickerson and hydrodistillation extracts, the injections were carried out in split mode and in splitless mode for the SPME extracts. Programming of the oven temperature varies in dependence of the analyzed extracts, however for most of the analyses, the conditions are the following: 80° C. up to 290° C. at 5° C./min.

Example III—Ethanol, P-Cymene, Thymol and Carvacol Analysis

For some extracts, it is also possible to titrate ethanol, p-cymene, thymol and carvacrol. The possibility of directly titrating p-cymene, thymol and carvacrol in the matrix was explored in the case of thyme and oregano infusions. A FFAP column 25 m long×0.32 mm internal diameter×0.3 μm film thickness was used. In particular, thyme and oregano infusions were analyzed by CPG/FID. 1 μL of each infusion was injected in an injector at 250° C. Temperature programming is the following: 40° C. to 220° C. (5 min) (5° C./min). The standards of p-cymene and thymol were injected as external standards to obtain calibration curves and as internal standard for identification. Titration of ethanol was also carried out by chromatography in gaseous phase combined with flame ionization (CPG/FID) for some infusions that were fermented from a calibration curve by directly injecting the solutions.

Example IV—Thyme Based Fermented Aqueous Extract

Material and methods. The plant selected is thyme (*Thymus vulgaris*) and in particular its flowering tops. The kefir grain is supplied by the Symbiotec laboratory. Once the quality control has been solved with respect to the plant or the part of the plant used, the aqueous extract (EA) is prepared: infusion of 10 g/L of *Thymus vulgaris* heated at a temperature of 85° C. during 20 minutes and filtered (Watman No. 2). The kefirated aqueous extract (EAK) is also prepared: infusion of 10 g/L of *Thymus vulgaris* heated at a temperature of 85° C. during 20 minutes and filtered. The EAK extract is cooled and 70 g/L of sugar is added, and this is followed by inoculation with a kefir grain at 27° C. during 30 days. When the parameters are in accordance with the standards provided (pH<4 and Brix<4), the fermentation is stopped and is filtered on paper (Watman No. 2) and then at 0.20 μm (cartridge filter).

Figure 5:
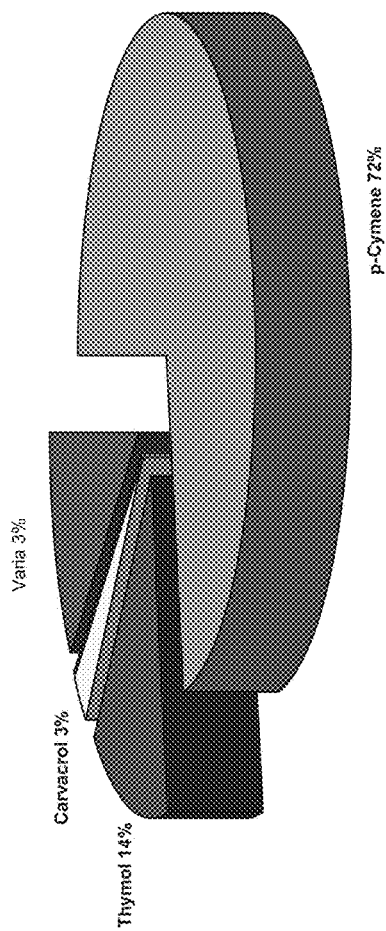
FIG. 5 shows the composition of an aqueous extract of non fermented *Thymus vulgaris*.
Figure 6:
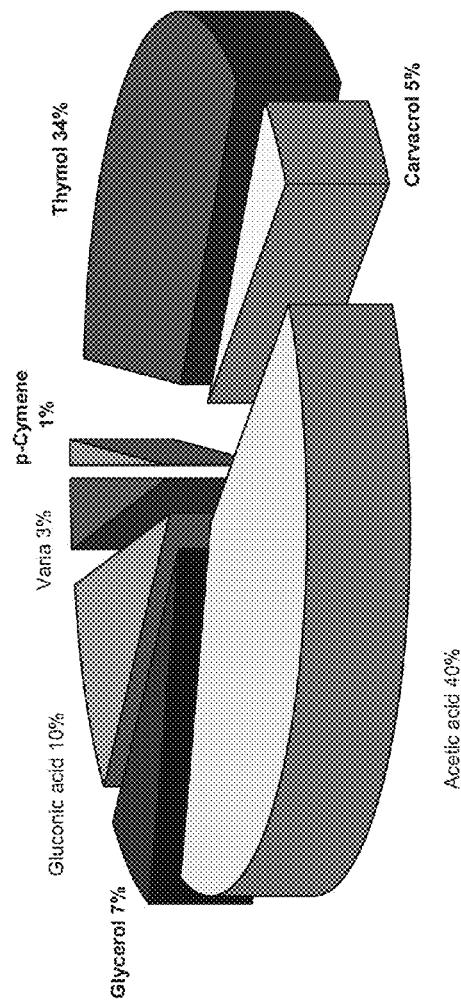
FIG. 6 shows the composition of an aqueous extract of kefirated *Thymus vulgaris*.

Identification of the components of the extracts. After aqueous extraction of *Thymus vulgaris* and identification by CPG/SM combined with an infra-red (IR), the composition in aromatic compounds shows a high proportion of para-cymene 72% (glycosylated) with 14% of thymol and 3% of carvacrol. The other components are a conglomerate of by-products (FIG. 5). After aqueous extraction of kefirated *Thymus vulgaris* and identification by CPG/SM combined with an IR, the composition in aromatic compounds has been modified, the thymol rate was multiplied by 2.5, the rate of carvacrol by 2 and para-cymene was reduced to 1%. Para-cymene is a precursor of thymol and of carvacrol. Kefication has therefore transformed the latter by bioconversion, preferably into thymol and carvacrol. Kefication causes the appearance of new compounds: acetic acid (40%), gluconic acid (10%) and glycerol (7%) (FIG. 6).

Comparison of aromatic profiles. The kefication of *Thymus vulgaris* is a good demonstration of the phenomenon of deglycosylation and bioconversion. Indeed, para-cymene cannot be converted into thymol if it has not previously been deglycosylated. Once deglycosylated, it is converted into thymol. The formation of acetic and gluconic acid as well as glycerol is attributed to kefication (FIG. 7). This synergy of the aromatic compounds formed by kefication is at the origin of the beneficial effects attributed to the kefirated plants and in particular, the antibacterial effect of *Thymus vulgaris*.

Example V—Valerian Based Fermented Aqueous Extract

Material and methods. The plant that is selected is valerian (*Valeriana officinalis* or valerian) and in particular its rhizomes. The kefir grain is supplied by the Symbiotec laboratory. The method of preparation of the valerian extract is a decoction and that of the thyme extract is an infusion. Once quality control has been resolved on the plant or the part of the plant used, the aqueous extract (EA) is prepared: decoction of 10 g/L of *Valeriana officinalis* heated to a temperature of 50° C. during 30 minutes and filtered (Watman No. 2). The kefirated aqueous extract (EAK): decoction of 10 g/L of *Valeriana officinalis* heated to a temperature of 50° C. during 30 minutes and filtered. The extract is cooled and 70 g/L of sugar are added, and the mixture is inoculated with a kefir grain at 27° C. during 30 days. When the parameters are in accordance with the anticipated standards (pH<4 and Brix<4), kefication is stopped and the mixture is filtered on paper (Watman No. 2) and then at 0.20 μm (cartridge filter).

Comparison of aromatic profiles. In the aqueous extract, bornyl acetate represents the main component with more than 26%, the other components being a conglomerate of molecules hard to isolate (69%) (FIG. 8). Kefication reduces the amount of bornyl acetate to 7% and redistributes the molecules hard to isolate (32%). Kefication multiplies by 3 the amount of valeric and valerinic acids which are major elements in the treatments of anxiety, stress and insomnia. The formation of acetic acid (21%), gluconic acid (7%) and glycerol (12%) shows that kefication took place with satisfaction. This kefication causes the appearance of caprylic and capric acids as well as a small amount of ethanol. This synergy of the components formed through kefication is responsible for the beneficial effects which are attributed to kefirated plants and in particular the anti-stress effect of *Valeriana officinalis*.

Example VI—Antibacterial Effect of Fermented Aqueous Extract of Thyme

During bacterial infections, therapeutics call for the use of antibiotics. However, in the last few years, high scale and some time inappropriate prescription of these antibiotics was followed by a selection of multi-resistant strains which result in hard to cure pathologies (e.g. nosocomial diseases). Research must therefore be directed towards new ways and in particular towards the plants which have always constituted a source of inspiration for new medicaments. Secondary metabolites (essential oils, polyphenols, etc.) which are produced by aromatic, medicinal or dietary plants have always been used as aromatizing and perfuming substances in perfumery, in the food and cosmetic industry and as antimicrobial agents in common medicine, in aromatherapy and in the food industry. The antibacterial activity of thyme when using dried flowering tops of *Thymus vulgaris* under different forms: aqueous extract (infusion), essential oil, kefirated aqueous extract have been compared.

Material and methods. The plant that was selected is thyme (*Thymus vulgaris*) and in particular its flowering tops. The kefir grain is supplied by the Symbiotec laboratory. Once the quality control with respect to the plant or part of the plant used, has been resolved, an aqueous extract of thyme is prepared: infusion of 10 g/L of *Thymus vulgaris* heated at a temperature of 85° C. during 20 minutes and filtered (Watman No. 2). Essential oil: hydrodistillation of *Thymus vulgaris*. Kefirated aqueous extract: infusion of 10 g/L of *Thymus vulgaris* heated at a temperature of 85° C. during 20 minutes and filtered. The extract is cooled and 70 g/L of sucrose is added and the mixture is inoculated with a kefir grain at 27° C. during 40 days. When the parameters comply with the anticipated standard, kefication is stopped and the mixture is filtered on paper (Watman No. 2) and then at 0.20 μm (cartridge filter). Preparation of the plant extract is identical for the kefirated and non kefirated products.

Strains of microorganisms. They come from clinical isolates provided by the laboratories of medical analyses of the Hôpital universitaire de Purpan-Toulouse (France). Resistant strains used: *Staphylococcus aureus, Pseudomonas aeruginosa, Escherichia coli, Aspergillus niger, Candida albicans, Bacillus cereus, Listeria monocytogenes, Enterococcus* sp.

Anti-bacterial test. By using microbiological techniques known in the art, it is possible to evaluate the antimicrobial activity of the extracts or of the essential oils of the plants (infusions, essential oils, kefirated plants, etc.). Evaluation of the antimicrobial activity according to the Comité de l'Antibiogramme de la Société Française de Microbiologie, and the Commission de la Pharmacopée Européenne. Technique of diffusion in agar+impregnated discs (6 mm diameter), Petri dish, bacteria: agar medium Müeller-Hinton, yeasts moulds: agar medium Sabouraud-dextrose, Inoculum: turbidity of Mac Farland 5 (105-108 CFU/ml), Calculation of the CMI (Minimum Inhibitor Concentration) by the method "Challenge test". Technique used: diffusion method.

Disc method. Discs of blotting paper, impregnated with extracts or essential oils to be tested, were placed on the surface of an agar medium, previously inoculated with a culture of the strain to be studied. Already upon application, the extracts or essential oils diffuse uniformly so much so that their concentrations are inversely proportional to the distance of the disc. After incubation, the discs are surrounded with circular inhibition zones which correspond to an absence of culture. The diameters of the inhibition zones are thereafter measured.

Results. Among all the clinical strains collected, the strains of *E. coli* were obtained from patients having urinary infections which were resistant against many families of antibiotics. The minimum inhibitor concentrations are consolidated in tables 1 and 2. The minimum inhibitor concentrations of the kefirated aqueous extract of *Thymus vulgaris* by comparison with the eight clinical strains are consolidated in FIG. 9.

In solid medium, the bacteriostatic action of the extracts and of the essential oil is represented by the appearance of inhibition zones around the discs. The diameter of the latter differs from one bacterium to another and varies from 2 mm to 40 mm. These inhibition zones determine a minimum inhibitor concentration.

Table 1 gives the sensitivity of the microorganisms tested with the aqueous extract (EAT), the kefirated aqueous extract (EAKT) and the essential oil of *Thymus vulgaris* (HET). The sensitivity of EAKT is apparent for a value of 1 μL/mL and is therefore very significant with respect to EAT whose values are higher than 200 μL/mL and with respect to HET whose values are higher than 8 μL/mL.

Table 2 confirms the preceding result and shows the strong inhibiting effect of the kefirated aqueous extract. The aqueous extract of thyme which has been tested is without inhibitor effect on most of the strains except at doses which exceed about 150 μl/mL (generally more than 200 μL/mL). The essential oil from thyme is effective against *Enterococcus* sp. *E. coli* and *Staphylococcus aureus* at values higher than 6 μL/mL. *Pseudomonas aeruginosa* and *Bacillus cereus* are more resistant, however the essential oil can inhibit them at doses lower than 18 μL/mL. The resistance of the strains of *Pseudomonas aeruginosa* against the essential oil tested is not surprising. In fact, this bacterium has an intrinsic resistance against biocidal agents which results from the nature of its external membrane. The latter is composed of lipopolysaccharides which constitute an impermeable barrier against hydrophobic compounds.

The kefirated aqueous extract from *Thymus vulgaris* shows an antibacterial activity against all the clinical strains tested at doses lower than 1 μl/mL (FIG. 9). The strain of *Pseudomonas aeruginosa* is sensitive towards this kefirated aqueous extract. Phenolic compounds are known to have an important antibacterial action, but this is not sufficient. It can be seen that the essential oil is less effective against some strains than the kefirated aqueous extract. The synergy of the components of the kefirated extract shows an increased antimicrobial potential and a sensitivity of the medical strains, even those which are multi-resistant against antibiotics (for example *E. coli* and *B. cereus*). The kefirated aqueous extract of *Thymus vulgaris* suggests the possibility of using it against infectious therapeutics and inter alia, against nosocomial pathologies, as a natural alternative to chemo-therapeutical agents whose spectrum of action is in continuous reduction. Also, it may be used in cosmetic as a preservative.

TABLE 1

Results of antimicrobial screening

| | μL/mL | 1 | 2 | 3 | 4 | 5 | 6 | 7 | 8 |
|---|---|---|---|---|---|---|---|---|---|
| EAKT | 0.5 | S | I | S | I | I | I | I | S |
| | 1 | S | S | S | S | S | S | S | S |
| | 2 | S | S | S | S | S | S | S | S |
| | 3 | S | S | S | S | S | S | S | S |
| | 4 | S | S | S | S | S | S | S | S |
| HET | 1 | R | R | R | R | R | R | R | R |
| | 2 | R | R | R | R | R | R | R | R |
| | 4 | R | R | I | R | R | R | R | R |
| | 6 | I | R | S | R | R | R | R | I |
| | 8 | S | R | S | R | R | R | R | S |
| EAT | 20 | R | R | R | R | R | R | R | R |
| | 50 | R | R | R | R | R | R | R | R |
| | 100 | R | R | R | R | R | R | R | I |
| | 150 | I | R | I | R | R | R | R | S |
| | 200 | S | R | S | R | R | R | R | S |

Legend of Table 1
R resistance,
I intermediate,
S sensitive
No Microorganisms:
1 *Staphylococcus aureus*,
2 *Pseudomonas aeruginosa*,
3 *Escherichia coli*,
4 *Aspergillus niger*,
5 *Candida albicans*,
6 *Bacillus cereus*,
7 *Listeria monocytogenes*,
8 *Enterococcus* sp

TABLE 2

Minimum inhibitor concentration of the aqueous extract of thyme (EAT), essential oil of thyme (HET) and kefirated aqueous extract of thyme (EAKT).

| | CIM (μL/mL) | | |
|---|---|---|---|
| Resistant clinical strains | EAT | HET | EAKT |
| *Staphylococcus aureus* | 200 | 7 | 0.5 |
| *Pseudomonas aeruginosa* | 300 | 18 | 0.8 |
| *Escherichia coli* | 180 | 6 | 0.3 |
| *Aspergillus niger* | 400 | 12 | 1 |
| *Candida albicans* | 400 | 15 | 1 |
| *Bacillus cereus* | 450 | 20 | 1 |
| *Listeria monocytogenes* | 300 | 17 | 0.6 |
| *Enterococcus* sp | 150 | 7 | 0.3 |

Example VII—Tests Made with Veal Calves

Preparation of a kefirated aqueous extract of oregano: infusion of 10 g/L of *Origanum vulgaris* heated at a temperature of 85° C. during 20 minutes and filtered. The EAK extract is cooled and 70 g/L of sucrose is added thereto ant it is inoculated with a kefir grain at 27° C. during 30 days. When the parameters comply with the anticipated standards (pH<4 and Brix<4), fermentation is stopped and the mixture is filtered on paper (Watman No. 2) and then at 0.20 μm (cartridge filter).

A mixture of thyme, such as defined in example IV, and oregano, fermented or kefirated, such as defined above, respectively 35/65 (v/v), is incorporated in the food at the rate of 10 ml per day and per calf starting on the fortieth day of life in the tested lot. On the other hand, the control calves did not receive this mixture of thyme and oregano, as fermented or kefirated.

The results obtained are described in table 3.

TABLE 3

Tests on veal calves

| Particulars | control | test |
|---|---|---|
| Duration of fattening in days | 129 | 126 |
| Number of calves | 68 | 68 |
| Number of dead | 4 | 0 |
| Average consumption of food per calf in kg | 298 | 292 |
| Daily average gain (GMQ) per calf in g | 1360 | 1399 |
| Consumption index (IC) | 1.70 | 1.65 |
| Average weight carcass per calf in kg | 145.54 | 146.25 |

Total consumption, during 126 days in the tested lot, per calf, of fermented or kefirated composition in ml: 1260.

Example VIII—Test with Calves in Battery

A mixture of thyme and oregano, fermented or kefirated, such as defined in example VII, respectivily 30/70 (v/v) is incorporated in the food at the rate of 0.25% (v/v) in the tested lot. On the other hand, the calves from the control lot did not receive this mixture of fermented or kefirated thyme and oregano.

The results obtained are described in tables 4 and 5.

TABLE 4 tests with calves in battery for a period of 148 days.

| Particulars | control | test |
|---|---|---|
| Duration of fattening in days | 148 | 148 |
| Number of calves | 65 | 65 |
| Number of dead | 1 | 1 |
| Average weight obtained per calf in kg | 501.66 | 506.06 |
| Typical gap | 45.84 | 28.15 |
| Daily average gain per calf (GMQ) in g | 2750 | 2780 |
| Average consumption index per calf (IC) | 1.57 | 1.55 |
| Average yield of carcasss per calf in % | 56.70 | 56.86 |

TABLE 5

Tests with calves in battery for a period of 68 days

| Particulars | control | test |
|---|---|---|
| Age at the start in days | 78 | 78 |
| Age at the end in days | 146 | 146 |
| Number of calves | 68 | 68 |
| Average weight gain for this period per calf in kg | 244 | 249 |
| Average daily gain per calf (GMQ) for this period in g | 3210 | 3280 |
| Average consumption index (IC) per calf for this period | 1.62 | 1.61 |
| Average yield of carcass per calf in % | 57.78 | 57.89 |

Example IX—Tests Made on Weaned Calves

A mixture of thyme and oregano, fermented or kefirated, as defined in example VII, respectively 35/65 (v/v) is incorporated in the food at the rate of 20 ml per day and per weaned calf until the 65th day for the lot tested. On the other hand, the calves of the control lot did not receive this mixture of fermented or kefirated thyme and oregano. On the 26th day, the calves from the tested and control lots are vaccinated.

The results obtained are described in table 6.

TABLE 6 tests with weaned calves

| Particulars | Average daily gain per calf (GMQ) in g/j | | |
|---|---|---|---|
| Duration in days | 0-26 | 26-75 | 0-75 |
| Control | 1417 | 1408 | 1411 |
| Test | 1448 | 1538 | 1507 |
| Average daily gain per calf difference between the tested lot and the control lot | 31 | 130 | 96 |

Total consumption, up to the sixty-fifth day, per calf, in the tested lot, of the fermented or kefirated composition in ml: 1300.

Example X—Test with Piglets During Post-Weaning

A mixture of fermented or kefirated thyme and oregano, such as defined in example VII, respectively 35/65 (v/v) is incorporated into the food at the rate of 1% (v/p) of the food for the tested lot. On the other hand, the piglets of the control lot did not receive this fermented or kefirated mixture of thyme and oregano.

The results obtained are described in table 7.

TABLE 7 tests with post-weaned piglets.

| Particulars | control | test |
|---|---|---|
| Duration of post-weaning in days | 43 | 43 |
| Number of piglets | 61 | 61 |
| Number of dead | 1 | 1 |
| Average weight obtained per piglet in kg | 23.66 | 24.71 |
| Typical gap | 3.75 | 3.16 |
| Average weight gain per piglet in kg | 15.81 | 16.45 |
| Daily average gain (GMQ) per piglet in g | 367.87 | 382.48 |

Total average consumption, during 43 days, per piglet, in the tested lot, of fermented or kefirated composition in ml: 300.

Example IX—Test with Butcher's Lambs

The death rate in a husbandry of more than 4000 lambs was as an average 4 deaths per day. It was decided to incorporate a mixture of fermented or kefirated thyme and oregano, as defined in example VII, respectively 35/65 (v/v) in the drinking water at the rate of 0.3% (v/v) for the whole husbandry. The results observed on a period of 15 days are described in table 8.

TABLE 8 tests with butcher's lambs

| Particulars | Period of treatment in days | Number of deads per day |
|---|---|---|
| Before treatment | | 4 |
| Start up | 0-1 | 2 |
| Treatment duration | 2-15 | 0 |

Total average consumption, during 15 days, per lamb, of fermented or kefirated composition: 105.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

The invention claimed is:

1. A method for the production of a fermented plant extract, said method comprising:
    providing a fermentable aqueous plant medium consisting of an aqueous plant extract, a fermentable carbohydrate source and a kefir grain, wherein the aqueous plant extract is from an extract selected from the group consisting of an agrimony extract, an alfalfa extract, an anise extract, an annato seed extract, an artichoke extract, an ashwagandha extract, an *astragalus* extract, a basil extract, a birch extract, a black pepper extract, a blackberry extract, a burdock extract, a celery extract, a chamomile extract, a cinnamon extract, a clove extract, a coffee extract, a coriander extract, a cumin extract, a dandelion extract, a *desmodium* extract, an elder flower extract, a *eucalyptus* extract, a euphrasia extract, a fennel extract, a garlic extract, a ginger extract, a *ginseng* extract, a green tea extract, a hibiscus extract, a holy basil extract, a hop extract, a lapacho extract, a lavender extract, a lemongrass extract, a maca extract, a matcha tea extract, a meadowsweet extract, a milk thistle extract, a neem extract, a nettle extract, a parsley extract, a passionflower extract, a peppermint extract, a plantain extract, a raspberry extract, a *rhodiola* extract, a rooibos extract, a rosemary extract, a sage extract, a savory extract, a turmeric extract, a violet leaf extract, a wheat grass extract, a white willow extract, a yarrow extract, a yerba mate extract, a lemonbalm extract, a puncture vine extract, a ginkgo extract, a saw palmetto extract, a Saint-John's wort extract, a cayenne extract, a *spirulina* extract, a kava kava extract, a kelp extract, a feverfew extract, a barley extract, an alfalfa extract, a licorice extract and combinations thereof; and
    incubating the fermentable aqueous plant medium under conditions to favor the conversion of the fermentable carbohydrate source to acetic acid to provide the fermented plant extract, wherein the conditions comprise: a fermentation duration of at least 20 days, a static fermentation, a fermentation temperature lower than 30° C., a fermentation pH<4, and a fermentation Brix<4.

2. The method of claim 1, wherein the conditions further comprise a batch fermentation, and/or a fermentation followed by a drying step.

3. A fermented plant extract produced by a method comprising:
    providing a fermentable aqueous plant medium consisting of an aqueous plant extract, a fermentable carbohydrate source and a kefir grain, wherein the aqueous plant extract is from an extract selected from the group consisting of an agrimony extract, an alfalfa extract, an anise extract, an annato seed extract, an artichoke extract, an ashwagandha extract, an *astragalus* extract, a basil extract, a birch extract, a black pepper extract, a blackberry extract, a burdock extract, a celery extract, a chamomile extract, a cinnamon extract, a clove extract, a coffee extract, a coriander extract, a cumin extract, a dandelion extract, a *desmodium* extract, an elder flower extract, a *eucalyptus* extract, a euphrasia extract, a fennel extract, a garlic extract, a ginger extract, a *ginseng* extract, a green tea extract, a hibiscus extract, a holy basil extract, a hop extract, a lapacho extract, a lavender extract, a lemongrass extract, a maca extract, a matcha tea extract, a meadowsweet extract, a milk thistle extract, a neem extract, a nettle extract, a parsley extract, a passionflower extract, a peppermint extract, a plantain extract, a raspberry extract, a *rhodiola* extract, a rooibos extract, a rosemary extract, a sage extract, a savory extract, a turmeric extract, a violet leaf extract, a wheat grass extract, a white willow extract, a yarrow extract, a yerba mate extract, a lemonbalm extract, a puncture vine extract, a ginkgo extract, a saw palmetto extract, a Saint-John's wort extract, a cayenne extract, a *spirulina* extract, a kava kava extract, a kelp extract, a feverfew extract, a barley extract, an alfalfa extract, a licorice extract and combinations thereof; and
    incubating the fermentable aqueous plant medium under conditions to favor the conversion of the fermentable carbohydrate source to acetic acid to provide the fermented plant extract, wherein the conditions comprise:
        a fermentation duration of at least 20 days,
        a static fermentation,
        a fermentation temperature lower than 30° C.,
        a fermentation pH<4, and
        a fermentation Brix<4.

4. The fermented plant extract of claim 3, comprising a high content of a deglycosylated active principle.

5. The fermented plant extract of claim 4, where the active principle is partially deglycosylated.

6. The fermented plant extract of claim 4, where the active principle is completely deglycosylated.

7. A composition comprising the fermented plant extract of claim 3 and an excipient.

8. The composition of claim 7, further comprising a product of milk origin or vegetable origin.

9. The composition of claim 8 being a powder.

* * * * *